(12) United States Patent
Schiffmann et al.

(10) Patent No.: US 8,410,101 B2
(45) Date of Patent: Apr. 2, 2013

(54) USE OF TETRAHYDROBIOPTERIN AS A MARKER AND A THERAPEUTIC AGENT FOR FABRY DISEASE

(75) Inventors: Raphael Schiffmann, Rockwell, TX (US); Teodoro G. Bottiglieri, Dallas, TX (US); Erland Arning, Fort Worth, TX (US); David F. Moore, Rockville, MD (US)

(73) Assignee: Baylor Research Institute, Dallas, TX (US)

( * ) Notice: Subject to any disclaimer, the term of this patent is extended or adjusted under 35 U.S.C. 154(b) by 254 days.

(21) Appl. No.: 12/757,420

(22) Filed: Apr. 9, 2010

(65) Prior Publication Data

US 2010/0260747 A1    Oct. 14, 2010

Related U.S. Application Data

(60) Provisional application No. 61/168,150, filed on Apr. 9, 2009.

(51) Int. Cl.
*A61P 43/00* (2006.01)
*G01N 33/20* (2006.01)

(52) U.S. Cl. ........ 514/249; 514/1.1; 436/98; 429/130.1; 424/9.2

(58) Field of Classification Search ............ 514/249, 514/1.1; 435/98; 429/130.1; 424/9.2
See application file for complete search history.

(56) References Cited

U.S. PATENT DOCUMENTS

| | | | |
|---|---|---|---|
| 4,774,244 | A | 9/1988 | Curtius et al. |
| 2002/0052374 | A1 | 5/2002 | Rabelink et al. |
| 2005/0197341 | A1 | 9/2005 | Woolf et al. |
| 2008/0075957 | A1 | 3/2008 | Kim et al. |
| 2008/0075959 | A1 | 3/2008 | Walker et al. |

OTHER PUBLICATIONS

Desnick et al. Annals of Internal Medicine, 2003, vol. 138, pp. 338-346.*
Breunig et al. Kidney international, vol. 63, Supplement 84 (2003) pp. S181-S185.*
Schafer et al. Drug Discovery Today 2008, 13 (21/22), 913-916.*
Horig et al. Journal of Translational Medicine 2004, 2(44).*
Costache, Heltianu, e al., "Endothelial Nitric Oxide Synthase Gene Polymorphisms in Fabry's Disease," Clinical Genetics, (2002), 61:423-429.
Moore, David F., et al., "Regional erebral Hyperperfusion and Nitric Oxide Pathway Dysregulation in Fabry Disease: Reversal by Enzyme Replacement Therapy," Circulation, (2001), 104;1506-1512.
Moore, David F., et al., "The Cerebral Vasculopathy of Fabry Disease," Journal of the Neurological Sciences 257, (2007), pp. 258-263.

* cited by examiner

*Primary Examiner* — Savitha Rao
(74) *Attorney, Agent, or Firm* — Fulbright & Jaworski L.L.P.

(57) ABSTRACT

Blood and tissue markers of the metabolic status, risk of health complications in Fabry disease patients and as a biomarker to follow the efficacy of treatment in animal models and patients with Fabry disease comprising tetrahydrobiopterin (BH4), precursors and metabolites of BH4, and other related co-factors is disclosed herein. The present invention further describes the use of BH4 therapy as a treatment option for Fabry disease to prevent, slow or reverses vascular cardiac and renal manifestations of Fabry disease.

5 Claims, 4 Drawing Sheets

USE OF TETRAHYDROBIOPTERIN AS A MARKER AND A THERAPEUTIC AGENT FOR FABRY DISEASE

CROSS-REFERENCE TO RELATED APPLICATIONS

This application claims priority to U.S. Provisional Application Ser. No. 61/168,150, filed Apr. 9, 2009, the entire contents of which are incorporated herein by reference.

TECHNICAL FIELD OF THE INVENTION

The present invention relates in general to the field of novel biomarkers and therapeutic agents and more particularly to the use of the co-factor tetrahydrobiopterin (BH4) as a biomarker and as a therapeutic agent in Fabry's disease.

STATEMENT OF FEDERALLY FUNDED RESEARCH

None

INCORPORATION-BY-REFERENCE OF MATERIALS FILED ON COMPACT DISC

None.

BACKGROUND OF THE INVENTION

Without limiting the scope of the invention, its background is described in connection with the use of tetrahydrobiopterin (BH4) in Fabry disease as: (i) a novel biomarker for diagnosis and of the severity of the disease, (ii) as a marker to follow the metabolic correction of the various therapies, and (iii) as a replacement therapy for Fabry disease.

U.S. Patent Application No. 20020052374 (Rabelink, et al., 2002) describes the use of at least folic acid or a folate and tetrahydrobiopterin (BH$_4$) or derivatives thereof for treating or preventing cardiovascular or neurological disorders by modulation of the activity of nitric oxide synthase (NOS) in the form of a pharmaceutical preparation suitable for influencing the nitric oxide (NO) level, particularly by modulation of the activity of nitric oxide synthase (NOS) by reducing superoxide (O$_2$) production and enhancing nitric oxide (NO) synthesis.

WIPO Publication Nos. 2008075959 & 2008075957 (Aerts, 2008) discloses a pathogenic factor allowing diagnosis of Fabry disease. In particular lyso-ceramide trihexosamide (lyso-CTH) has been found to function as a diagnostic marker for Fabry disease and an improved therapy for Fabry disease based on the identification of the pathogenic factor in the plasma.

United States Patent Application No. 20050197341 (Woolf et al., 2005) teaches a method of treating, reducing, or preventing pain and/or the consequences or development of a peripheral nerve lesion in a mammal by administering a composition that reduces the tetrahydrobiopterin (BH4) biological activity in an amount sufficient to treat, reduce, or prevent pain or the exacerbation of a peripheral nerve lesion due to overproduction of BH4.

U.S. Pat. No. 4,774,244 (Curtius et al., 1988) teaches the use of L-erythro-5,6,7,8-tetrahydrobiopterin, L-sepiapterin, 1',2'-diacetyl-5,6,7,8-tetrahydrobiopterin and 6-methyl-5,6,7,8-tetrahydropterin can be used for the therapeutic treatment of patients with Parkinson's disease and of patients with depression.

SUMMARY OF THE INVENTION

The present invention describes the measurement of BH4 levels in blood and tissues. The measured levels serve as markers of the severity of Fabry disease and risk for complications and further serve as a marker to follow the metabolic correction of various therapies of Fabry disease. The present invention further describes BH4 replacement as a useful therapy for Fabry disease.

In a primary embodiment the present invention is a method of diagnosing Fabry's disease comprising the steps of: (i) collecting a sample from a subject suspected of having Fabry's disease, (ii) comparing the levels of at least one of tetrahydrobiopterin (BH4), a precursor or a metabolite and related co-factors in the sample from the subject suspected of having Fabry's disease with that of a normal subject not having Fabry's disease and (iii) determining whether the subject has Fabry's disease based on a statistically significant decrease of the at least one of tetrahydrobiopterin (BH4), precursors, metabolites and related co-factors in the sample between the subject and the normal subject. The sample for measuring the levels of at least one of tetrahydrobiopterin (BH4), a precursor or a metabolite and related co-factors is a biological fluid sample, and the analytical technique used for measuring the levels of at least one of tetrahydrobiopterin (BH4), precursors, metabolites and related co-factors is a high pressure liquid chromatography (HPLC) method.

In one aspect of the present invention the related co-factors comprise organic co-factors, flavin containing co-factors, heme containing co-factors, inorganic co-factors, metal ion containing co-factors, iron-sulfur clusters, or any combinations thereof. In another aspect the measured levels of the at least one of tetrahydrobiopterin (BH4), precursors, metabolites and related co-factors in the subject suspected of having Fabry's disease is lower by 20%, 30%, 40%, 50%, 60%, 80%, 90% and 100% when compared to the normal subject.

Another embodiment of the present invention is directed towards a method of monitoring the efficacy of a therapeutic intervention on a subject suffering from Fabry's disease. The method involves, administering one or more pharmaceutical compositions to the subject at one or more pre-defined intervals, wherein the pharmaceutical composition comprises one or more therapeutic agents against Fabry's disease, collecting a sample from the subject, comparing the levels of at least one of tetrahydrobiopterin (BH4), a precursor or a metabolite and related co-factors in the sample from the subject suspected with that of the same subject prior to the commencement of the therapeutic intervention and determining whether the therapeutic intervention is effective based on the comparison of the measured levels of the at least one of tetrahydrobiopterin (BH4), precursor or metabolite and related co-factors before in the sample from the subject before and after the commencement of the therapeutic intervention.

The sample collected from the subject is a biological fluid sample. In related aspects the method comprises the steps of terminating or continuing the therapeutic intervention based on the comparison of the measured levels of the at least one of tetrahydrobiopterin (BH4), precursor or metabolite and related co-factors. In a further aspect the method involves modifying the therapeutic intervention based on the comparison of the measured levels of the at least one of tetrahydrobiopterin (BH4), precursor or metabolite and related co-factors before and after the commencement of the therapeutic intervention, wherein the modification comprises an increase or a decrease in a dose, a frequency or both of the one or more pharmaceutical compositions In one aspect the therapeutic intervention comprises enzyme replacement therapies, pain medications, dialysis, organ transplantation, diet modifications, or any combinations thereof. In another aspect the at least one of tetrahydrobiopterin (BH4), precursors, metabolites and related co-factors is determined using high pressure liquid chromatography (HPLC) method. In yet another aspect the related co-factors comprise organic co-factors, flavin containing co-factors, heme containing co-factors, inorganic co-factors, metal ion containing co-factors, iron-sulfur clusters, or any combinations thereof. In a further aspect the measured levels of the at least one of tetrahydrobiopterin (BH4), precursor or metabolite and related co-factors in the subject undergoing the therapeutic intervention is greater than the measured level of the at least one of tetrahydrobiopterin (BH4), precursor or metabolite and related co-factors in the same subject prior to the commencement of the therapeutic treatment.

In an important embodiment of the present invention describes a pharmaceutical composition for treating Fabry's disease in a diseased subject comprising: a therapeutically effective amount of at least one of a tetrahydrobiopterin (BH4), a precursor, a derivative, or salts thereof sufficient to treat Fabry's disease dissolved, dispersed, or suspended in an aqueous or a non-aqueous solvent, one or more optional related co-factors, proteins, antibodies, pain medications and other pharmaceutically active agents dissolved, dispersed, or suspended in an aqueous or a non-aqueous solvent, and one or more optional excipients, fillers, diluents, extended or controlled release agents, bulking agents, antiadherents, binders, lubricants, preservatives or any combinations thereof.

In a related aspect the pharmaceutical composition is infused, administered subcutaneously, intravenously, peritoneally, orally, and intramuscularly. In one aspect the pharmaceutical composition increases the measured levels of the at least one of tetrahydrobiopterin (BH4), precursor or a metabolite and related co-factors in a sample of a subject taking the pharmaceutical composition when compared to the sample of a subject not taking the pharmaceutical composition.

In yet another embodiment the present invention describes a method of treating Fabry's disease in one or more subjects comprising the steps of: (i) identifying the one or more subjects in need of treatment against Fabry's disease and (ii) administering one or more pharmaceutical compositions comprising a therapeutically effective amount at least one of tetrahydrobiopterin (BH4), a precursor, a derivative or salts thereof and one or more related co-factors sufficient to treat Fabry's disease.

In a further extension of the above embodiment the method further comprises the steps of monitoring the progression of Fabry's disease following the administration of the pharmaceutical composition, wherein the monitoring comprises measuring the levels of the at least one of tetrahydrobiopterin (BH4), precursor or metabolite and related co-factors following treatment and comparing the measured levels with the measured levels prior to the treatment. In related aspects the method further comprises the step of terminating or continuing the treatment based on the comparison of the measured levels of the at least one of tetrahydrobiopterin (BH4), precursor or metabolite and related co-factors before and after the commencement of the treatment.

In yet another aspect the method further comprises the step of modifying the treatment based on the comparison of the measured levels of the at least one of tetrahydrobiopterin (BH4), precursor or metabolite and related co-factors before and after the commencement of the treatment; wherein the modification comprises an increase or a decrease in a dose, a frequency or both of the one or more pharmaceutical compositions.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1A:
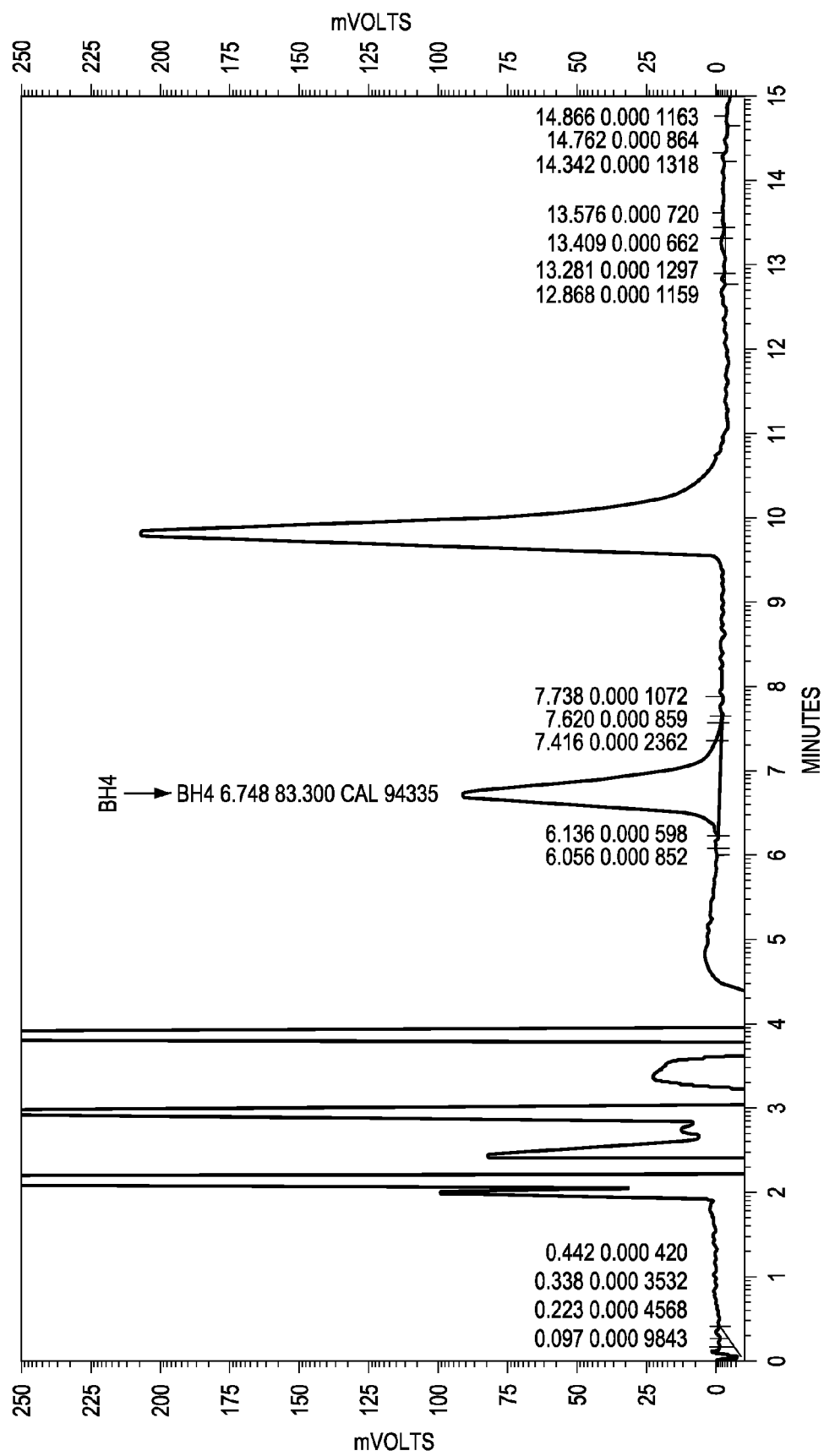
FIG. 1A is a HPLC chromatogram showing the BH4 peak in a standard solution of BH4.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below.

Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein the term "X-linked disorder" refers to disorders are caused by mutations in genes on the X chromosome. X-linked disorders can be either dominant (for example, Rett syndrome, Incontinentia Pigmenti type 2, Aicardi Syndrome, Klinefelter's syndrome, etc.) or recessive (for example, Hemophilia A, Duchenne muscular dystrophy, Lesch-Nyhan syndrome, male pattern baldness, red-green color blindness, etc,)

The term "glycosphingolipid" denotes a carbohydrate-containing derivative of a sphingoid or cermaid, wherein the carbohydrate residue is attached by glycosidic linkage to O-1 of the sphingoid. The term "sphingoid" denotes a long-chain aliphatic amino alcohol. Unsaturated derivatives of sphingoids are defined in terms of the location and configuration of each olefinic center.

The term "α-galactosidase" as used herein refers to the glycoside hydrolase enzyme that hydrolyses the terminal α-galactosyl moieties from glycolipids and glycoproteins. As used herein, the term "enzyme" refers generally to proteins that catalyze biochemical reactions. These "biopolymers" include amide-linked amino acids and typically have molecular weights of 5,000 or greater. A compound for which a particular enzyme catalyzes a reaction is typically referred to as a "substrate" of the enzyme. In general, six classes or types of enzymes (as classified by the type of reaction that is catalyzed) are recognized. Enzymes catalyzing reduction/oxidation or redox reactions are referred to generally as EC 1 (Enzyme Class 1) Oxidoreductases. Enzymes catalyzing the transfer of specific radicals or groups are referred to generally as EC 2 Transferases. Enzymes catalyzing hydrolysis are referred to generally as EC 3 hydrolases. Enzymes catalyzing removal from or addition to a substrate of specific chemical groups are referred to generally as EC 4 Lyases. Enzymes catalyzing isomeration are referred to generally as EC 5 Isomerases. Enzymes catalyzing combination or binding together of substrate units are referred to generally as EC 6 Ligases.

The term "enzyme replacement therapy" (ERT) refers to a medical treatment replacing an enzyme in a subject or a patient in whom that particular enzyme is deficient or absent. Usually this is done by giving the patient an intravenous (IV) infusion containing the enzyme (for example patients suffering from some lysosomal diseases like Gaucher disease, Fabry disease, MPS I, MPS VI and Glycogen storage disease type II). ERT does not "treat" the underlying disease, only the symptoms.

As used herein the term "biomarker" refers to a specific biochemical in the body that has a particular molecular feature to make it useful for diagnosing and measuring the progress of disease or the effects of treatment. For example, common metabolites or biomarkers found in a person's breath, and the respective diagnostic condition of the person providing such metabolite include, but are not limited to, acetaldehyde (source: ethanol, X-threonine; diagnosis: intoxication), acetone (source: acetoacetate; diagnosis: diet/diabetes), ammonia (source: deamination of amino acids; diagnosis: uremia and liver disease), CO (carbon monoxide) (source: $CH_2Cl_2$, elevated % COHb; diagnosis: indoor air pollution), chloroform (source: halogenated compounds), dichlorobenzene (source: halogenated compounds), diethylamine (source: choline; diagnosis: intestinal bacterial overgrowth), H (hydrogen) (source: intestines; diagnosis: lactose intolerance), isoprene (source: fatty acid; diagnosis: metabolic stress), methanethiol (source: methionine; diagnosis: intestinal bacterial overgrowth), methylethylketone (source: fatty acid; diagnosis: indoor air pollution/diet), O-toluidine (source: carcinoma metabolite; diagnosis: bronchogenic carcinoma), pentane sulfides and sulfides (source: lipid peroxidation; diagnosis: myocardial infarction), $H_2S$ (source: metabolism; diagnosis: periodontal disease/ovulation), MeS (source: metabolism; diagnosis: cirrhosis), and $Me_2S$ (source: infection; diagnosis: trench mouth).

The term tetrahydrobiopterin (BH4) or a derivative thereof, refers to all natural and unnatural stereoisomeric forms of tetrahydrobiopterin, pharmaceutically compatible salts thereof and any mixtures of the isomers and the salts. The term tetrahydrobiopterin also includes any precursors of tetrahydrobiopterin, especially 7,8-dihydrobiopterin. (6R)-tetrahydrobiopterin is a naturally occurring cofactor of the aromatic amino acid hydroxylases and is involved in the synthesis of the three common aromatic amino acids tyrosine, phenylalanine, tryptophan and the neurotransmitters dopamine and serotonin. It is also essential for nitric oxide synthase catalyzed oxidation of L-arginine to L-citrullin and nitric oxide. Tetrahydrobiopterin is also involved in many other biochemical functions.

As used herein, the term "treatment" or "treating" means any administration of a compound of the present invention and includes (1) inhibiting the disease in an animal that is experiencing or displaying the pathology or symptomatology of the diseased (i.e., arresting further development of the pathology and/or symptomatology), or (2) ameliorating the disease in an animal that is experiencing or displaying the pathology or symptomatology of the diseased (i.e., reversing the pathology and/or symptomatology).

The term "plasma" as used herein refers to the proteinaceous fluid comprising suspended red blood cells, white blood cells, and platelets. It makes up about 55% of the total blood volume.

It is the intravascular fluid part of extracellular fluid. It is mostly water (90% by volume) and contains dissolved proteins, glucose, clotting factors, mineral ions, hormones and carbon dioxide (plasma being the main medium for excretory product transportation).

The term "high performance liquid chromatography" (HPLC), as used herein, refers to the separation of molecules under high pressure (around 500-3500 psi) in a column filled with a matrix (between 3 and 50 microns). Molecules are separated according to their physical properties such as their size, shape, charge, hydrophobicity, and affinity for other molecules. In general, the components to be separated are distributed between two phases: a stationary phase bed and a mobile phase which percolates through the stationary bed. A mixture of various components enters a chromatography process, and the different components are flushed through the system at different rates. These differential rates of migration as the mixture moves over adsorptive materials provide separation. Repeated sorption/desorption acts that take place during the movement of the sample over the stationary bed determine the rates. The smaller the affinity a molecule has for the stationary phase, the shorter the time spent in a column.

Fabry disease is an X-linked disorder of glycosphingolipids that is caused by the deficiency of α-galctosidase A. Fabry disease is a risk factor for developing a systemic vasculopathy, progressive kidney disease, many cardiac complications and ischemic stroke. It is a chronic disorder over decades that has no good biomarkers.

Previous researchers by the present inventors has indicated that there is an increased production of non-nitric oxide (NO) reactive species (such as superoxide) especially in blood vessel wall and vascular endothelial cells that likely results from a dysfunction of endothelial nitric oxide synthase (eNOS). BH4 is an essential factor for normal eNOS activity. In the event of BH4 deficiency, eNOS switches from producing NO to generating oxygen free radicals that increase oxidant stress in blood vessels leading to vascular damage.

BH4 levels were found to be deficient in a mouse model system of chronic pressure load in the heart BH4 supplementation reversed the cardiac abnormalities. Enzyme replacement therapy is the only available specific therapy for Fabry disease. However, it has limited efficacy especially regarding the cardiac manifestations and it does not prevent strokes. There are no biomarkers that are useful to assess the progression of the disease or that can serve as surrogate markers for the assessment of efficacy of therapeutic interventions.

In studies conducted in the present invention the inventors found a marked deficiency of BH4 in the blood (34% reduction) and the heart (48% reduction) in a mouse model of Fabry disease that is a complete knockout of GLA (the gene that codes for α-galctosidase A).

Analytical method for the detection of BH4 in plasma and tissues using an animal model: A well-described mouse model was used for the detection of BH4 in plasma and the tissues (Ref.). The mice were descendents of an original colony developed at the National Institute of Neurological Disorders and Stroke with a genetic background C57/b16 X 129/SVJ. Five month old male mice were used. Age and sex-matched control mice of the same genetic background were used.

Principle: The analytical method relies on reversed phase HPLC separation of BH4 with electrochemical detection. The current generated on the reduction cell is monitored and used to determine the BH4 concentration in biological samples based on the calibration of the system with external standards.

Equipment: The HPLC pump and the refrigerated autosampler were obtained from Shimadzu (LC-10AT VP series, SIL-10A), The electrochemical detector, the analytical cell and the conditioning cell were obtained from ESA (ESA Coulochem II EC Detector, ESA Model 5011A Analytical Cell, and ESA Model 5021 Conditioning Cell respectively). The HPLC Column and the Guard column were obtained from Phenomenex (Synergi Hydro-RP 250×3.0 mm 4μ and Synergi Hydro-RP 4×3.0 mm 4μ respectively). The HPLC was controlled by Shimadzu software: Class VP Version 7.4.

Chemicals & Reagents: All the chemicals and reagents used in the analysis were purchased from Sigma/Aldrich Chemical Co. Tetrahydrobiopterin ((6R)-5,6,7,8-tetrahydro L-biopterin dihydrochloride, 0.4 M Perchloric Acid, Dithioerythritol, Diethylenetriamine pentaacetic acid (DETAPAC), Sodium Acetate Trihydrate, Citric Acid, and Ethylenediaminetetraacetic acid (EDTA,2H$_2$O).

Running Conditions: The flow rate was set at 0.5 ml/min and the injection volume was 5 μl. The column was maintained at ambient room temp. The chromatographic run time was 15 minutes.

Preparation of Reagents and Standards: The mobile phase comprises of 6.8 g of Sodium Acetate, 1.05 g of Citric Acid, 20 mg of EDTA and 100 mg of dithioerythritol dissolved in 800 ml. of Milli-Q water in a 1 liter glass container. The solution was transferred to a 1000 ml volumetric flask and the volume adjusted to 1 liter to make up the mobile phase. The mobile phase was degassed with helium for 10 minutes and the top of the container was tightly wrapped with aluminum foil. The solution was transferred to the HPLC mobile phase container Deproteinization Solution A is prepared by dissolving 20 mg DTE and 20 mg DETAPAC in 10 ml of PCA (0.4M) followed by sonication for 10 minutes for complete dissolution.

Diluent Solution B was prepared by dissolving 20 mg DTE and 20 mg DETAPAC in 10 ml of Milli-Q water followed by sonication for 10 minutes for complete dissolution.

BH4 calibration standard was prepared fresh on each day of use. A 1:2 (V/V) of sample diluent/deproteinization solution was added for final of 0.266 M PCA (dilution A). Stock solutions of BH4 were diluted as follows. 100 μl of 250 μM BH4 was added to 900 μl of fresh 0.266 M PCA DTE/DETAPAC solution and mixed well by vortexing (standard B). Add 100 μl of standard B to 900 μl of fresh 0.266 M PCA DTE/DETAPAC solution and mix well by vortexing. A working Standard Solution of (83.3 nM BH4) was prepared by adding 100 μl of 2.5 μM BH4 standard to 900 μl of fresh 0.266 M PCA DTE/DETAPAC solution and mixed well by vortexing. Add 50 μl of 250 nM standard to 100 μl of diluent solution B and mixed well by vortexing. The working standards can be stored in refrigerator at 4° C. for up to 8 hours.

Preparation of plasma samples: Blood obtained by cardiac puncture using tuberculin syringes containing 5 mg of EDTA and immediately transferred to a collection tube contain 2 mg DTE and 2 mg DETAPAC. Process blood to obtain plasma by centrifugation at 8000 rpm for 5 minutes at 4° C. To 50 μL plasma or working standard solution (250 nm) add 100 μL deproteinization solution A and mixed well by vortexing, followed by centrifugation at 14,800 rpm for 5 minutes at 4° C. 50 μl of plasma supernatant is added to 100 μl of diluent solution B and mixed well by vortex. 5 μl of the plasma sample is injected into the HPLC system.

Preparation of liver, kidney and heart tissues: Tissues obtained from mice euthanized by asphyxiation with carbon monoxide were immediately frozen by place on dry ice and stored at −80° C. until time of analysis. On the day of analysis the tissues were homogenized tissues using a 1:5 dilution with deproteinization solution A and centrifuged at 14,800 rpm for 5 minutes at 4° C. 100 μL of clear supernatant was removed and added to 100 μl of sample diluent solution B and mixed well by vortexing followed by injection of 5 μl into the HPLC system.

Calculation of BH4 concentration: The system was calibrated on external 83.3 nM BH4 standard. To calculate the plasma concentration the value from read out is multiplied by 9 to give the final value in nmol/L. To calculate the concentration in the tissues the value from read out is multiplied by 10 to give the value in nmol/L followed by division by 1000 to give the value in nmol/g.

Figure 1B:
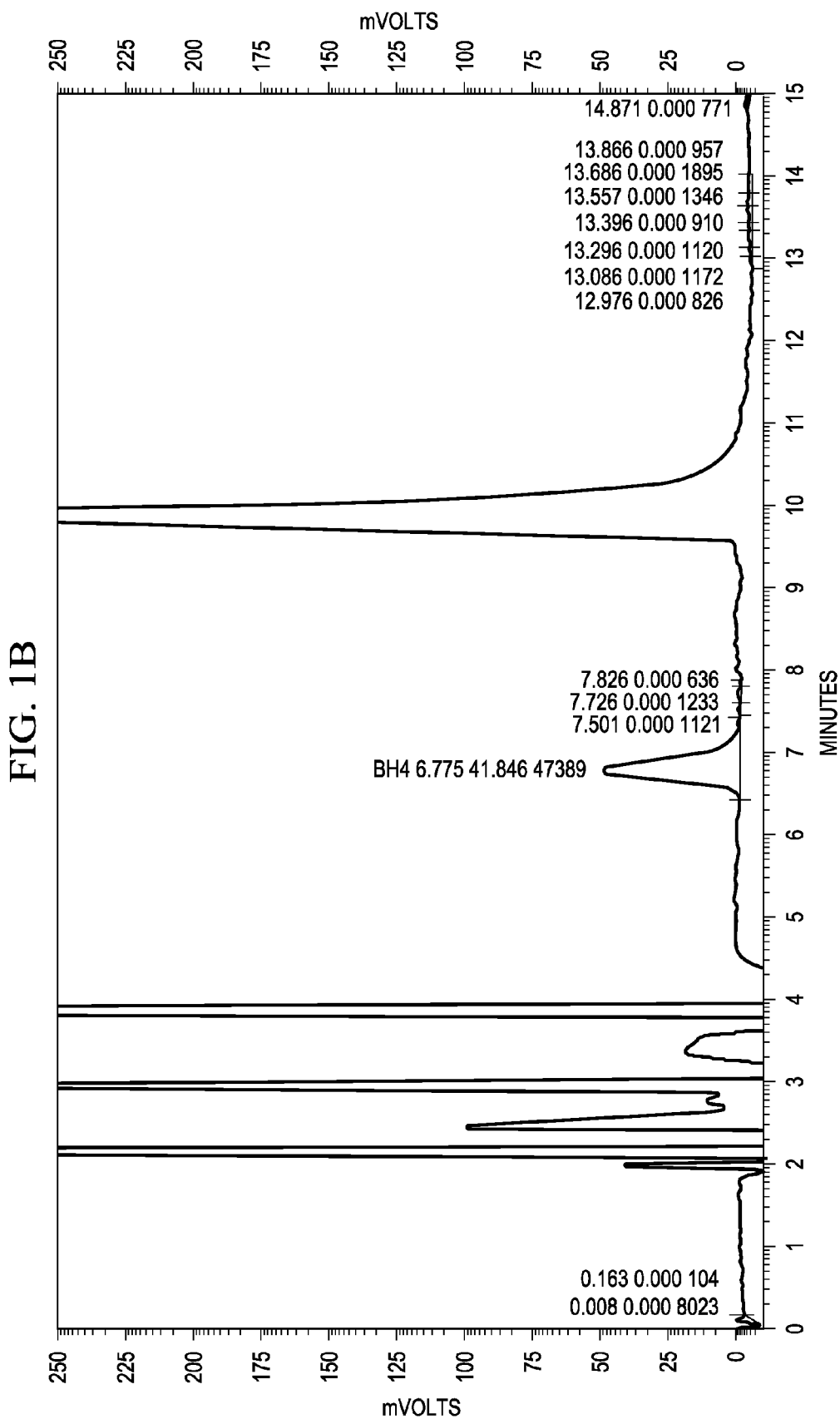
FIG. 1B is a HPLC chromatogram showing the BH4 peak in a mouse plasma sample.
Figure 2:
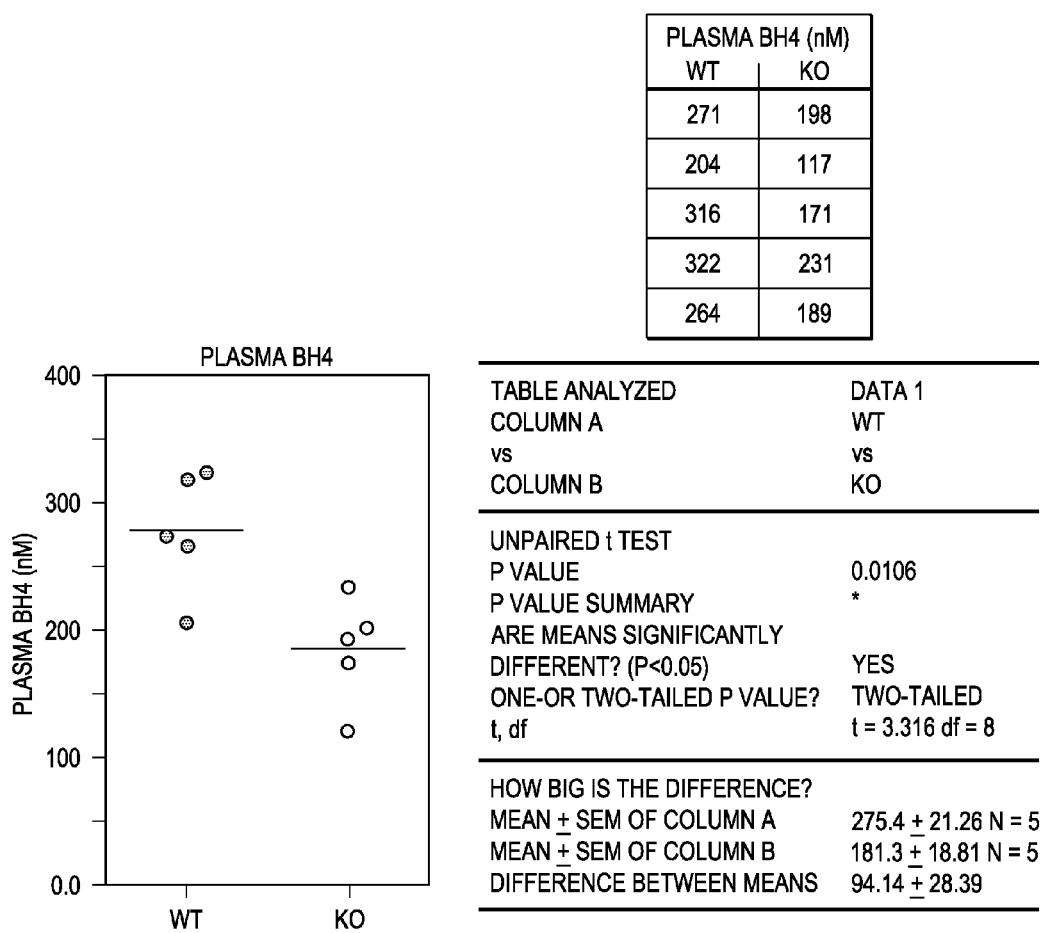
FIG. 2 is a statistical analysis and a scatter plot of the levels of BH4 in WT and KO mouse plasma samples.
Figure 3:
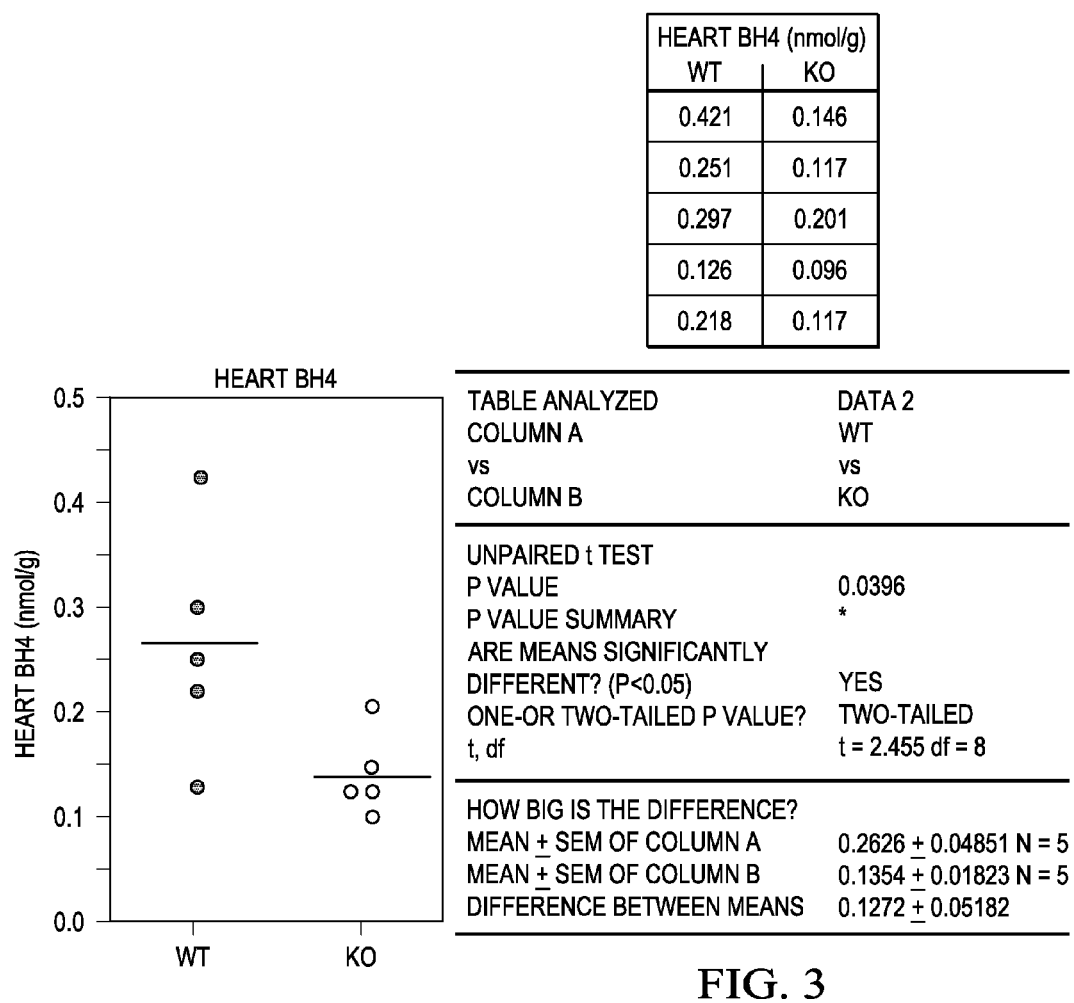
FIG. 3 is a statistical analysis and a scatter plot of the levels of BH4 in WT and KO mouse heart tissue samples.

FIGS. 1A and 1B are HPLC chromatograms showing the BH4 peak in a standard solution of BH4 and the BH4 peak in a mouse plasma sample. FIGS. 2 and 3 show a statistical analysis and scatter plot of the levels of BH4 in WT and KO mouse plasma and heart tissue samples, respectively.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

U.S. Patent Application No. 20020052374: Pharmaceutical preparation containing at least folic acid or a folate and tetrahydrobiopterin (bh4) or derivatives thereof used for treating or preventing cardiovascular or neurological disorders by modulating of the activity of nitric oxide synthase (nos).
WIPO Publication Nos. 2008075959: Diagnostic marker for Fabry disease.
WIPO Publication Nos. 2008075957: Treatment of Fabry disease.
U.S. Patent Application No. 20050197341: Methods for treating pain.
U.S. Pat. Publication No. 4,774,244: Use of pterin derivatives.

What is claimed is:

1. A method of treating Fabry's disease in one or more subjects comprising the steps of:
    identifying the one or more subjects in need of treatment against Fabry's disease; and
    administering one or more pharmaceutical compositions comprising a therapeutically effective amount of tetrahydrobiopterin (BH4) in a therapeutically effective amount sufficient to treat Fabry's disease.

2. The method of claim 1, further comprising the steps of monitoring the progression of Fabry's disease following the administration of the pharmaceutical composition, wherein the monitoring comprises measuring the levels of tetrahydrobiopterin (BH4) following treatment and comparing the measured levels with the measured levels prior to the treatment.

3. The method of claim 2, further comprising the step of terminating the treatment based on the comparison of the measured levels of tetrahydrobiopterin (BH4) before and after the commencement of the treatment.

4. The method of claim 2, further comprising the step of continuing the treatment based on the comparison of the measured levels of tetrahydrobiopterin (BH4) before and after the commencement of the treatment.

5. The method of claim 2, further comprising the step of modifying the treatment based on the comparison of the measured levels of tetrahydrobiopterin (BH4) before and after the commencement of the treatment, wherein the modification comprises an increase or a decrease in a dose, a frequency or both of the one or more pharmaceutical compositions.

* * * * *